United States Patent [19]

Thomas

[11] Patent Number: 5,026,387
[45] Date of Patent: Jun. 25, 1991

[54] METHOD AND APPARATUS FOR ULTRASONIC SURGICAL CUTTING AND HEMOSTATIS

[75] Inventor: Alan E. Thomas, Ocean City, N.J.

[73] Assignee: Ultracision Inc., Smithfield, R.I.

[21] Appl. No.: 492,491

[22] Filed: Mar. 12, 1990

[51] Int. Cl.$^5$ ............................................. A61B 17/32
[52] U.S. Cl. ................................... 606/169; 606/171; 310/316; 604/22; 128/24 AA
[58] Field of Search ................ 604/22; 606/167–171; 310/316; 128/24 A; 433/86

[56] References Cited

U.S. PATENT DOCUMENTS

| | | | |
|---|---|---|---|
| 3,489,930 | 1/1970 | Shoh | 310/316 |
| 3,526,792 | 9/1970 | Shoh | 310/316 |
| 4,156,157 | 5/1979 | Mabille | 310/316 |
| 4,227,110 | 10/1980 | Douglas et al. | 310/316 |
| 4,371,816 | 2/1983 | Wieser | 318/316 |

Primary Examiner—Stephen C. Pellegrino
Assistant Examiner—Steven J. Shumaker
Attorney, Agent, or Firm—Nixon & Vanderhye

[57] ABSTRACT

A power control arrangement for an ultrasonic surgical device such as a scalpel which provides power on demand in response to the continuous or periodic sensing of the loading condition (tissue contact or withdrawal) of the blade such that the device goes from a low power, idle state to a selectable high power, cutting state automatically depending on whether the scalpel is or is not in contact with tissue. A third, high power coagulation mode is manually selectable with automatic return to an idle power level when the blade is not in contact with tissue.

34 Claims, 4 Drawing Sheets

METHOD AND APPARATUS FOR ULTRASONIC SURGICAL CUTTING AND HEMOSTATIS

BACKGROUND AND SUMMARY OF THE INVENTION

The invention relates generally to ultrasonic surgical instruments and processes and more particularly to methods and apparatus for facilitating the performance of surgical procedures such as cauterization of large blood vessels or simultaneous soft tissue dissection and coagulation of small vessels through the use of a precisely controlled ultrasonically vibrating scalpel.

The use of an electric scalpel or a laser as a surgical instrument with the dual function of simultaneously effecting the incision and hemostasis of soft tissue by cauterizing tissues and blood vessels while cutting are known. Electrosurgery using such instruments, however, employs very high temperatures to achieve coagulation, causing vaporization and fumes as well as splattering, which increases the risk of spreading infectious diseases to operating room personnel. Additionally, the use of such instruments often results in relatively wide zones of thermal tissue damage.

Cutting, shattering and drilling instruments with ultrasonic drive mechanisms in non-surgical fields are known. Additionally, conventional surgical instruments utilizing the capacity of ultrasonic vibrations to cut or shatter a wide range of living tissues such as the soft tissue found in cataract surgery as well as bone chips or the like in orthopedics, are also well known.

One of the problems associated with such ultrasonic cutting instruments is uncontrolled or undamped vibrations and the heat as well as material fatigue resulting therefrom. In an industrial application, such problems can be dealt with by simply turning off the instrument when it is not in contact with the workpiece. In an operating room, however, such practice is neither practical nor acceptable. That is to say, in the latter environment precise cutting and heating control must be provided in order to prevent thermal tissue injury and scalpel fracture.

Known devices have attempted to solve the heating problem by the inclusion of cooling systems with heat exchangers or the like. In one known system, for example, the ultrasonic cutting and tissue fragmentation system requires a cooling system augmented with a water circulating jacket as well as requiring means for irrigation and aspiration of the cutting site. Another system uses ultrasonic cutting of soft tissue wherein the ultrasonic cutting instrument requires the delivery of cryogenic fluids to the cutting blade.

In accordance with my invention, there is provided a method and apparatus for overcoming the foregoing and other problems associated with conventional electric, laser and ultrasonic surgical incising/cautery devices. The exemplary embodiments disclosed include the "power on demand" control feature of causing a surgically sharp cutting instrument, such as a scalpel blade, or other surgical instrument such as a dull cautery blade to automatically shift its operation between an unloaded or idle state and a loaded or cutting state, and vice versa, depending on whether or not the instrument is in contact with tissue.

Such contact can be determined by monitoring parameters such as ultrasound driving current or impedance in response to the dampening of the vibration which occurs upon tissue contact.

When in the loaded or cutting state the blade is supplied with longitudinal back and forth movement at ultrasonic frequencies and at a selectable cutting power level. Such ultrasonic activation of the blade, although increasing the efficiency of cutting, generates heat as the mechanical energy of the accelerating moving blade is converted to thermal energy. Under such circumstances, the localized heat creates a very narrow zone of thermal coagulation that reduces or eliminates bleeding. The zone is narrow or limited since temperature elevations are transient and heat is produced only at the narrow contact point of the blade edge. Moreover, since the power level is selectable as a percentage of full power, a range of cutting/coagulation control levels is available to the surgeon for selection depending on the nature of the tissue encountered as well as other factors.

When in the unloaded or idle state, power is still transmitted to the instrument for the purpose of monitoring operating parameters, but such power is at a reduced or low level, thereby minimizing heat build-up. Elimination of such heat build-up is important since at high power levels the vibrating blade will become very hot when not in contact with tissue or other physiological medium if allowed to continue to run in air at high power. When the entire blade is hot, the zone of thermal injury is less controlled and excessive thermal tissue injury results in an extended healing period as well as excessive scarring. Furthermore, excessive heating of the blade resulting from undamped ultrasonic vibration may lead to stress fractures in the instrument and injury to nearby personnel.

Accordingly, it is an important feature of my disclosed exemplary methods and apparatus that power be continuously applied to the device so that operating parameters can be continuously or periodically monitored for detected changes in response to damping of the vibrations upon tissue contact or detected changes in response to undamped vibrations or oscillations upon withdrawal of the blade from tissue contact. Detection of such changes are used for the automatic application of a controlled amount of power to the ultrasonic surgical instrument, such as the application of an increased selected level of cutting power to the blade in going from the idle state to a cutting state when tissue contact is sensed, and the rapid reduction in power applied to the blade when withdrawal of such contact is sensed.

In a further exemplary embodiment, the disclosed methods and apparatus include a coagulation mode wherein power of a selectably high level is applied for a short time for coagulating relatively large bleeders. This mode is implemented, for example, by the user selecting the duration of high coagulation power application and the time of initiation through the use of a switch or the like and thereafter tamponading the bleeder with the back or edge of a blade.

In a still further exemplary embodiment, the disclosed methods and apparatus include a system wherein the selection of operating parameter threshold levels is such that the surgical device will not inadvertently switch from the idle state to the loaded or cutting state when the blade is immersed in blood or other body fluid but not in contact with tissue. Such selection of threshold levels eliminates splattering and ultrasonic atomization of the fluids and assures delivery of cutting power only when the scalpel blade makes contact with tissue in the act of cutting or coagulating. Careful selection of appropriate system operation parameters must also be made in determining the point at which the system is to be powered down to the idle or unloaded state in order to prevent overheating of the acoustic system; such overheating occurs when high power is delivered to the surgical instrument in an undamped condition.

These and further objects and advantages of the present invention will become apparent upon reference to the following specification, appended claims and drawings.

DETAILED DESCRIPTION OF THE DRAWINGS

Figure 1:
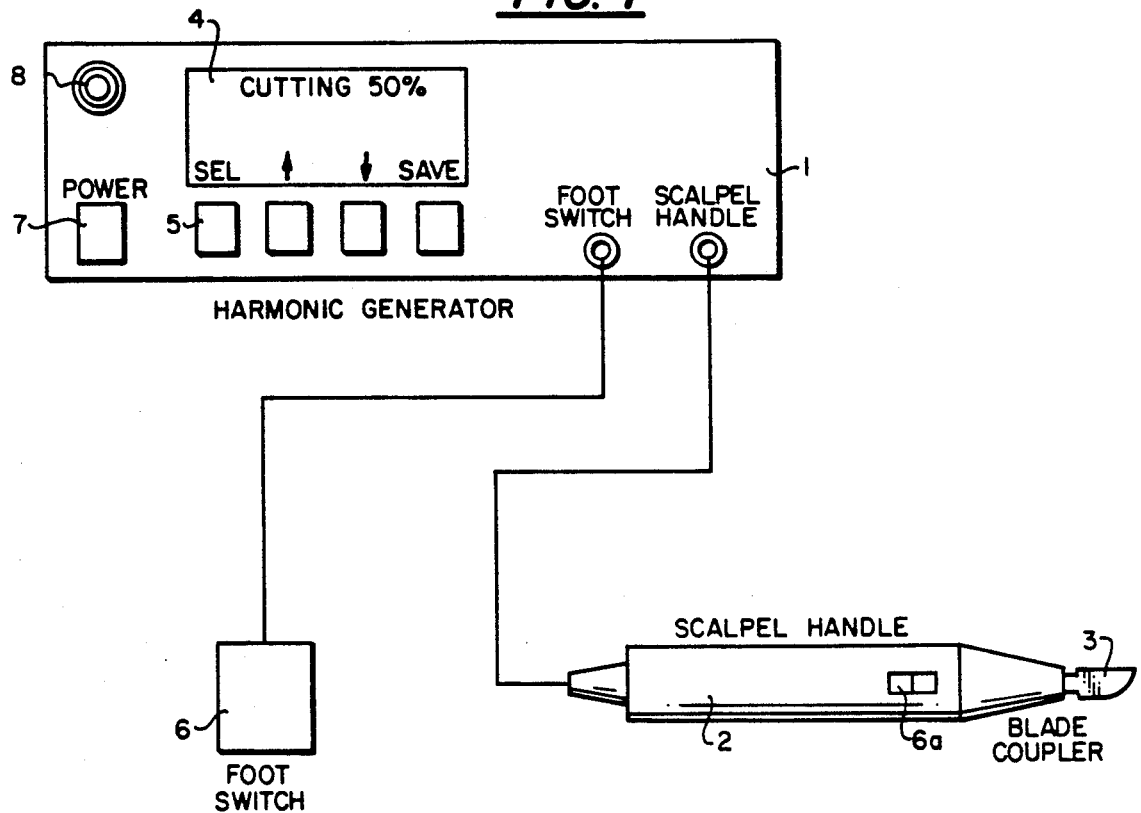
FIG. 1 is a perspective illustration of an ultrasonic surgical cutting and hemostasis system in accordance with an exemplary embodiment.
Figure 3:
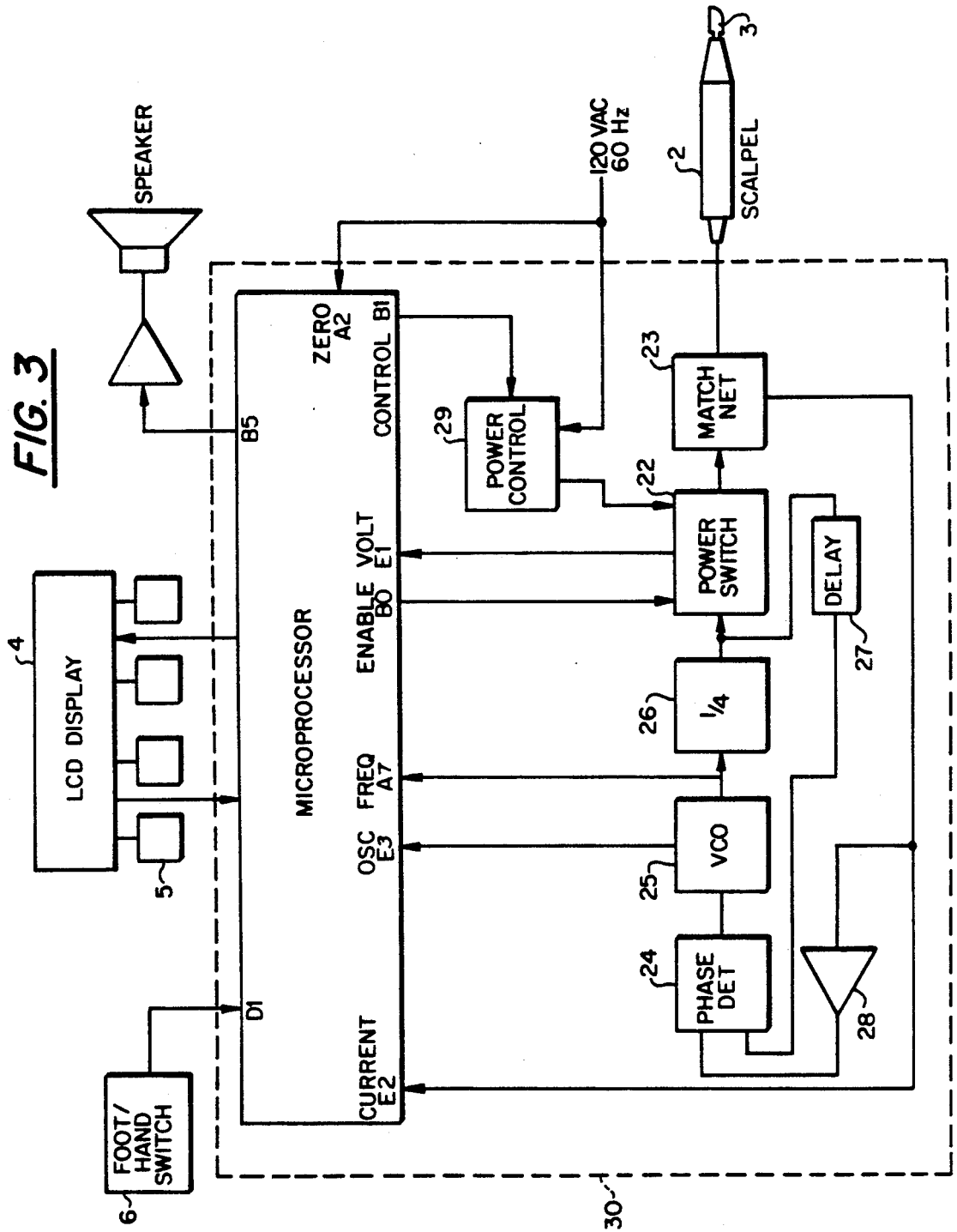
FIG. 3 is a system diagram illustrating the harmonic generator of the ultrasonic device and additionally shows details of the power control feature of the system.

As generally shown in FIG. 1, a harmonic generator 1 provides electrical energy to the hand assembly 2 which imparts ultrasonic longitudinal movement to a surgical device such as a sharp scalpel blade 3 used for simultaneous dissection and coagulation. The hand assembly may also provide such movement to other types of surgical instruments, such as one used for coagulation alone. The generator includes a liquid crystal display device 4 indicating, for example, the selected cutting power level as a percentage of maximum cutting power. The power selection level as well as other functions, such as coagulation mode duration, may also be selected by appropriate manipulation of the switches or push buttons generally indicated at 5 in response to a menu appearing on the display. For safety and durability, the hand assembly is connected to the harmonic generator by a coaxial cable. Also, detachably connected to the harmonic generator is a foot switch 6 for causing activation of the device in a coagulation operation mode. Alternatively and preferably a switch 6a is incorporated in the handle 2 in place of switch 6. Although not illustrated in FIG. 1, an audio output indicative of mode changes and present mode is generally indicated by the speaker of FIG. 3, which is responsive to the microprocessor included in the harmonic generator.

With the power switch 7 turned on as would be indicated by power indicator lamp 8, energy is continuously applied by the harmonic generator to the ultrasonic hand assembly either at a reduced or low level when the surgical blade is not in contact with tissue, or at a relatively high level which is a selectable percentage of maximum cutting power; a level that is maintained when the blade is in contact with tissue. Power applied to the ultrasonic hand assembly will cause a surgical device such as a scalpel blade to vibrate longitudinally at approximately 55 kHz, and the amount of longitudinal movement will vary proportionately with the amount of driving power applied, as adjustably selected by the user.

When relatively high cutting power is applied, the blade is designed to move longitudinally in the range of about 20 to 200 microns and preferably in the range of 30 to 40 microns at the aforementioned vibrational rate. Such ultrasonic activation of the scalpel blade generates heat as the extremely high blade acceleration through tissue converts the mechanical energy of the moving blade to thermal energy in a very narrow and localized area. Such localized heat creates a narrow zone of coagulation which will reduce or eliminate bleeding in small vessels, such as those less than one millimeter in diameter.

Such coagulation known as "white thermal coagulation results when the tissue temperature is high enough to cause protein denaturation. Denatured protein forms a rigid quasi-glutinous or "white" coagulum similar to the white of a hard-boiled egg. Hemostasis is achieved as the sticky coagulum seals blood vessels.

The degree of increased cutting efficiency as well as the degree of hemostasis obtained will, of course, vary with the level of driving power applied, the cutting rate of the surgeon as well as the nature of the tissue type and vascularity involved.

Figure 2:
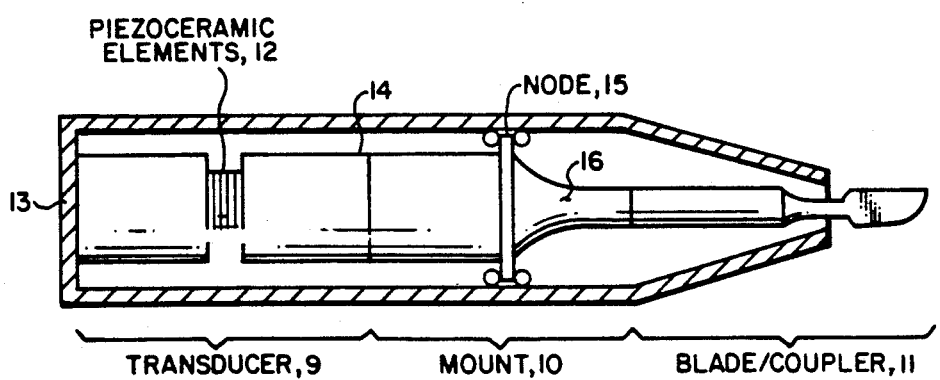
FIG. 2 is a schematic perspective view of the ultrasonic scalpel hand assembly shown partially in cross-section.

As illustrated in more detail in FIG. 2, the ultrasonic hand assembly 2 houses an acoustic system for converting electrical energy to mechanical energy that results in longitudinal vibrational motion; said acoustic system comprises a transducer 9, a mounting device 10 and a surgical device 11, such as a scalpel blade and holder. The transducer includes a stack of ceramic piezoelectric elements 12 with a motionless node at the center of the stack. As illustrated, the stack is sandwiched between two aluminum cylinders 13 and 14. Additionally, the transducer is fixed to the mounting device in a permanent manner with the mounting device attached to the housing at another motionless node by an integral ring 15.

The mounting device, transducer and blade/coupler are designed and fabricated to oscillate at the same resonant frequency with each element tuned accordingly such that the resulting length of each such element is one-half wavelength. Expansion of the piezoelectric ceramic elements results in the initiation of motion in the acoustic system of the transducer.

The ends of the transducer achieve maximum motion with the center of the stack constituting a motionless node when the transducer is driven with a high voltage such as 300 volts and low current expending approximately 100 watts at the transducers' resonant frequency. As illustrated in FIG. 2, the mounting device which is driven mechanically by the transducer and fixed to the housing at a motionless node through the use of an integral ring 15 includes an acoustic amplification horn 16 formed on the blade/coupler 11 side of the motionless node. Longitudinal back and forth motion is amplified as the diameter of the mounting device decreases. Although the blade and coupler vibrate (approximately 55,000 cycles per second) in phase with the transducer, the blade/coupler and the mounting means which drives it vibrate at 180° out of phase with respect to the transducer. The amplification horn as well as the blade/coupler, which is shaped and dimensioned so as to amplify blade motion and provide harmonic vibration in resonance with the rest of the acoustic system, obtain a maximum back and forth motion of preferably from 30 to 40 microns resulting in extremely high blade acceleration through tissue at the noted vibrational rate. Although the above range is preferred, a range of 20 to 200 microns is contemplated.

Although the ultrasonic hand assembly is re-usable subsequent to being sterilized by the user, the blade/coupler is intended to be sharpened, sterilized and separately packaged for a single use only. Additional details pertaining to the blade/coupler may be obtained by reference to copending application Ser. No. 07/448,862 entitled "Apparatus and Methods for Attaching and Detaching an Ultrasonic Actuated Blade/Coupler and An Acoustical Mount Therefor".

Turning to a consideration of the system diagram as illustrated in FIG. 3, the harmonic generator 30 provides the power to drive the acoustic system of the ultrasonic hand assembly at the desired frequency and power level setting. A microprocessor 21, which is integral with the harmonic generator may be a programmed Motorola Model No. 6811, for example, and is used to monitor for the appropriate power parameters and vibratory frequency as well as causing the appropriate power level to be provided in either the cutting or coagulation operating modes. Additionally, it maintains the appropriate low power level when in the idle mode.

As previously noted, controls 5 are provided for the purpose of allowing the operator to adjust the power level to be applied in the cutting mode so that simultaneous cutting and small vessel coagulation of the desired level is obtained whenever the scalpel touching tissue condition is detected. Such selectable power levels may also be applied to other surgical instruments which require such vibratory motion when tissue contact is sensed. The coagulation mode on the other hand is obtained by a momentary pressing of the foot/hand switch which activates the ultrasonic hand assembly at a selectable high power level for the length of time selected by the user by way of the input setting means 5. In the latter mode, however, the processor may be programmed to shorten the length of time that power is applied, as set by the user, when the blade is not in contact with tissue or other physiological medium since the undamped vibrating blade or other instrument will become very hot in a short period of time at such power levels. Moreover, when the entire blade/instrument is hot, the zone of thermal injury is less controlled and may result in excessive thermal tissue injury.

In the coagulation mode, which is useful for sealing blood vessels up to 4 millimeters in diameter, coagulation may be obtained by compressing the vessel to be sealed and thus eliminate the heat sink effect of blood flowing through the vessel. "Coaptive coagulation" is the use of compression to tamponade or block the flow and "coapt" the vessel wall, followed by the application of heat. The vessel wall is sealed as coagulum keeps the collapsed vessel closed. The disclosed ultrasonic scalpel combines the principles of both coaptive and white thermal coagulation. That is to say, to coagulate large vessels, the surgeon applies direct pressure and high ultrasonic power with the unsharpened edge of the blade or instrument, which generates sufficient heat to seal the vessel.

Figure 4A:
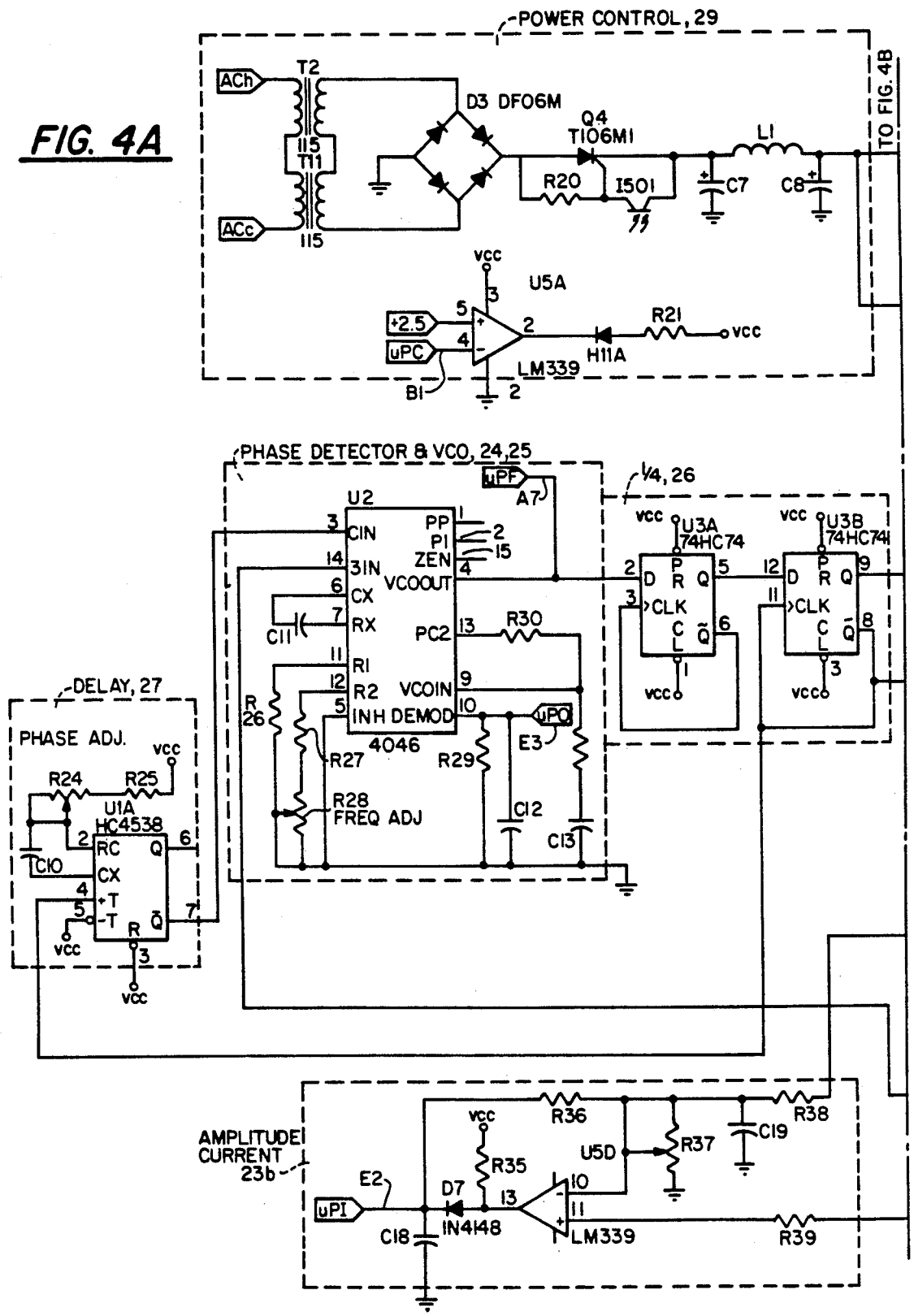
FIGS. 4A and 4B are more detailed schematic diagrams of the harmonic generator and the power control feature.
Figure 4B:
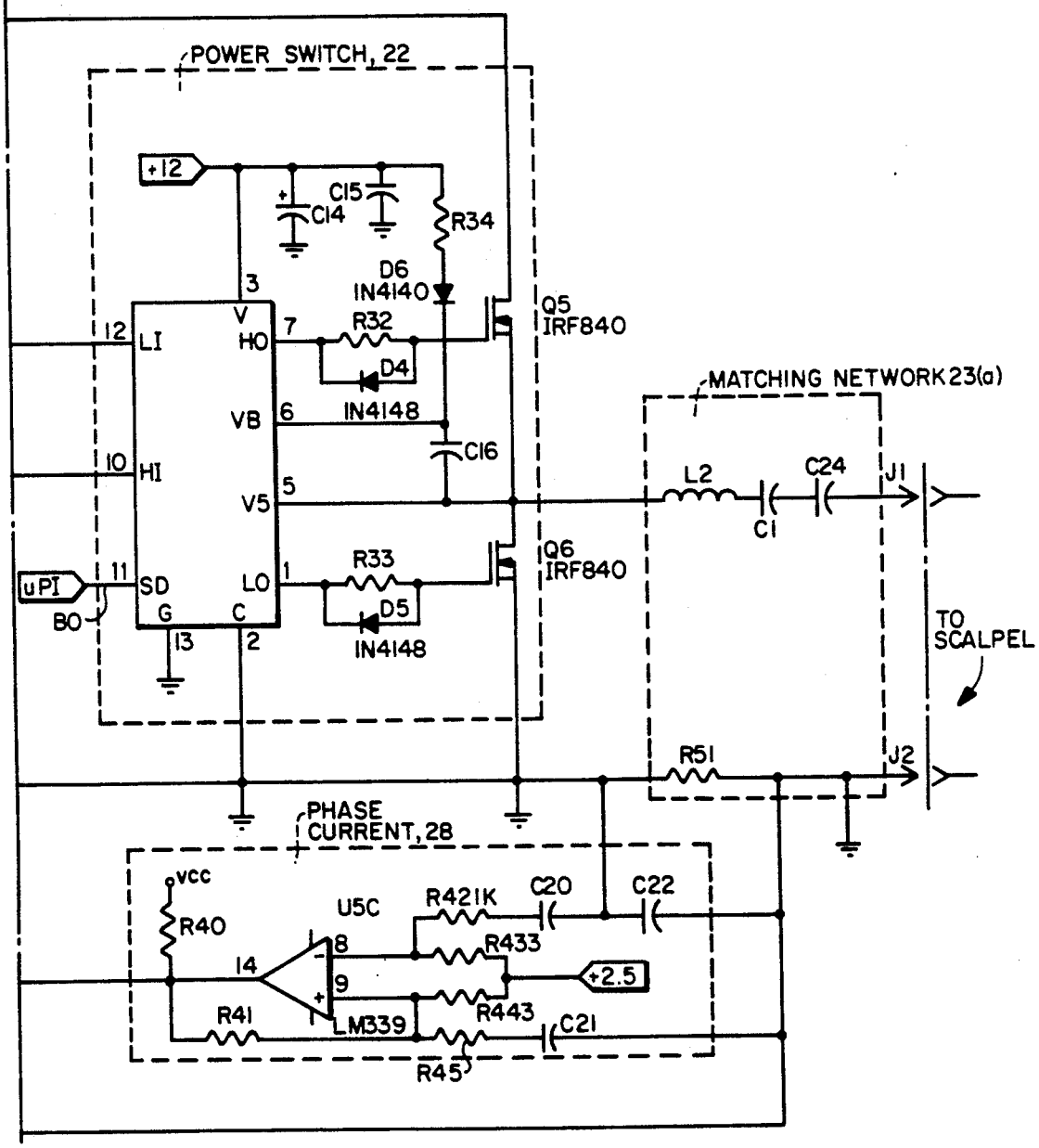

In operation the power switch 22 supplies electrical power to the ultrasonic hand assembly 2 by way of a matching network 23. As shown in FIG. 4, the power switch may be constructed of an integrated driver circuit with a half bridge FET switching circuit (Q5, Q6) connected to the matching network 23 which comprises a LC filter for converting the square wave from the power switch to a sine wave as well as including a resistor for determining the ultrasound driving current which is monitored for power control purposes.

The microprocessor 21 senses a target voltage, as set by the user, which is based upon a percentage of full power and compares the target voltage with the output voltage sensed at the power switch, which is forwarded to the microprocessor at input E1. Upon determination of the difference in the two voltages, the processor then changes the phase delay time at control output B1 which in turns acts as a phase control for a silicon controlled rectifier (SCR) such as Q4 of power control 29. The SCR, which, as shown in FIG. 4, is connected to the FET's of the power switch 22, has its duty cycle increased or decreased by the processor depending on whether the sensed output voltage is below or above the target value, respectively. In addition to sensing the zero crossings and output voltage, for example, the microprocessor also senses other operating conditions such as frequency at input A7 as well as the current at input E2 so that if the operating conditions are not within prescribed limits the enable signal at processor output at B0 is not present, and the power switch accordingly cannot be enabled.

Frequency control for causing the frequency of the generator to match the harmonic frequency of the ultrasonic acoustic system is obtained through the use of a phase lock loop comprising phase detector 24 for comparing the phase of the output driving current and voltage signals with the error signal obtained from the phase detector being used to control the voltage controlled oscillator to thereby generate the desired frequency. The voltage controlled oscillator output connected to the microprocessor at E3 is a voltage which is proportional to the generated frequency and is used for monitoring purposes to determine if the frequency is within the proper operating range.

The frequency produced by the voltage controlled oscillator is actually four times the desired ultrasonic drive frequency and is subsequently divided by four by divider element 26 which includes two cascaded flip-flops. The output of divider 26 drives the power switch. By generating four times the desired frequency at the output of VCO 25 and connecting it to an event counter in the microprocessor at A7 a much more accurate determination of the frequency may be obtained every 0.25 seconds for measuring and displaying purposes. Additionally, the 4f and divider selection guarantees a 50% duty cycle for the power switch 22.

The microprocessor at input E2 monitors the ultrasonic drive current detected at the matching network. Measurements are made and stored in the processor every 8.33 milliseconds. When the ultrasonic scalpel is turned on, the microprocessor executes a short initialization calibration routine where the ultrasonic scalpel is powered to the selected cutting power as well as the high coagulating power level so as to measure and store the current values sensed at the matching network when the scalpel is vibrating undamped in air at these power settings. Although at known voltage settings the driving point impedance may be selected as a parameter for determining when to switch modes such as from an idle mode to a run mode or vice versa, in a preferred embodiment the drive current is the parameter monitored for mode changing purposes.

Subsequent to the calibration process, which is repeated each time the power setting is changed, the instrument is in an idle mode wherein although the driving power is at a low setting and blade motion is not detectable, a small amount of drive current is delivered to the instrument at approximately 55 kHz. Thus, even when in an idle or non-cutting mode, ultrasonic power is delivered to the transducer for monitoring purposes.

The "power on demand" feature of the disclosed system involves the detection of tissue contact by the instrument which causes a damping of the vibration of the blade and the automatic system response whereby the microprocessor powers up the ultrasonic scalpel to the preselected cutting power thus obtaining simultaneous tissue incision with "white thermal coagulation" of small blood vessels.

The damping of the ultrasonic vibrations caused by tissue contact results in a reduction of the measured driving current and, as previously noted, may serve as the sensed parameter for automatically powering up from an idle or ready mode to a cutting mode. Immersion of the blade in a pool of blood or other body fluid will also result in a damping of the ultrasonic vibrations and a decrease in the current. Powering up under the latter circumstances, however, would cause splattering and ultrasonic atomization and the resulting increased risk of spreading infectious disease to operating room personnel.

Although percentages will vary somewhat depending on the specific instruments selected and the conditions of use, it has been experimentally determined that the drop in driving current in most instances when the blade contacts tissue is approximately 5% or more of the idle current; whereas, immersion of the scalpel in body fluid without tissue contact would cause less than a 5% drop in the current at the matching network. It has additionally been experimentally determined that the ideal threshold level at which the selected cutting-/coagulation power is triggered on may vary from slightly less than 5% such as 3% up to about a 25% drop in idle current, depending on the tissue type and vascularity as well as the level of pressure applied by the surgeon. The latter factor is a matter of individual preference. In most instances, however, a 10% threshold value is preferred. Accordingly, the target value is selectable and stored by the microprocessor as the threshold value for powering up to a cutting mode and will preferably involve about a 10% reduction in idle current. Thus, high power will be delivered to the blade only when it is in contact with tissue in the act of cutting or coagulating.

Once the blade is powered up to a selectable cutting power level or is operated in a coagulation mode by operation of the foot/hand switch, it is necessary for the microprocessor to continue to monitor the current at the matching network at 8.33 millisecond intervals since the surgical instrument will become very hot when it is not in contact with tissue or other physiological medium. Such extreme heating of a blade, for example, must be avoided since it in combination with undamped ultrasonic vibration causes stress, cracking and blade fracture as well as excessive thermal tissue injury when the entire blade is hot.

Such excessive heating would be especially prevalent in the coagulation mode where the system powers up to a selectable high power level. Accordingly, the microprocessor stores an upper threshold current value which in a preferred embodiment is equal to about 95% of the maximum measured calibration current value. As aforementioned, the microprocessor in the cutting or coagulating modes continues to monitor the drive current at the matching network and upon detecting a rise in current to 95% (or greater) of the stored calibration current value (indicating that the blade is no longer in contact with tissue) will cause the system to power down to the idle or ready state. Thus, excessive heating of the blade and its deleterious effects are avoided. In this regard it is to be noted that although a coagulation mode may be instituted by the operation of the foot switch 6 or the hand switch 6a for a period of time selectable by the user through the operation of input means 5, the microprocessor will nevertheless continue to monitor current during the set time period and will cause the system to power down to the idle or ready mode when the non-tissue contact condition is detected by a rise in current to the stored threshold value.

FIG. 4 illustrates exemplary details of components 22 through 29 of FIG. 3 with appropriate designations of the connections to the microprocessor. Such details are merely exemplary, and it is submitted that other implementations will occur to those skilled in the art without departing from the scope of the inventive teachings found herein.

As previously noted, the microprocessor may, for example, be a Motorola Model No. 6811. Implementation of the exemplary claimed embodiments may be obtained with the disclosed combination of elements with appropriate instructions stored in the programmable read-only memory of the microprocessor. A source code outline for each of the idle, cut and coagulation modes is included in a appendix which follows. Additionally, included are outlines for the initialization and interrupt routines or subroutines.

In the idle mode, for example, voltage, current and frequency values are measured and stored as well as being range compared for a determination of whether all parameters are within proper operational limits. Current is additionally repeatedly measured for a determination of whether the selected threshold decrease is present so that the scalpel will shift to the cut mode when the condition is detected. Additional subroutines are included such as "READ TIMER" wherein stored values for idle current and the like are updated to correct for drift when the device has not changed modes for a predetermined period of time. As another example, the "READ FOOT/HAND SWITCH" routine would allow the surgeon to set new cutting or coagulation values without touching input selectors 5 thus maintaining a sterile field. That is to say, through the indicated use of the foot or hand switch a menu may be caused to appear on the liquid crystal display 4 with selection of new operating values obtained through the operation of the same switch.

Similar routines are found in the outlines or flow charts for the "CUT" and "COAG" modes. For example, in addition to measuring and determining whether voltage, current and frequency are within operational limits such that the system is enabled, the cut and coagulation values or "targets" are read for subsequent comparison with measured values and appropriate adjustment of the stored trigger times for the SCR of the power control circuit. Additional sub-routines are included, for example to give audible indications of the present operating mode.

---

APPENDIX

INITIAL MODE
SET TARGET

APPENDIX (set all parameters and store in EEPROM)
Scale the A/D reference - VRH
SEE DISPLAY SIMULATION
SUB VREG (verify voltage regulation)
    SUB AIR CUT CURRENT
        (at the target voltage)
    SUB AIR COAG CURRENT
        (at the coag voltage)
IDLE MODE
MEASURE VOLTAGE
SUB AVG
STORE VOLTAGE
SUB TRIGGER
MEASURE OSC
SUB AVG
STORE OSC
    IF LOW ERROR
    IF HIGH ERROR
READ FREQ
    IF LOW ERROR
    IF HIGH ERROR
READ TIMER
    IF 5 MIN. SUB AIR CURRENT
        (to re-establish base line current
        in air) (for cut and coag)
    INCREMENT IDLE TIMER (see notes on
        INCREMENT CUT TIMER)
READ FOOT/HAND SWITCH
    IF DOUBLE CLICK GOTO INITIAL MODE
    (menu - go through all options)
SUB VREG (verify voltage regulation)
    MEASURE CURRENT
    SUB AVG
    STORE IDLE CURRENT
        IF LOW ERROR
        IF HIGH ERROR
        IF 5% DECREASE GOTO CUT MODE
CUT MODE
READ TARGET
MEASURE VOLTAGE
SUB AVG
STORE VOLTAGE
SUB TRIGGER
MEASURE OSC
SUB AVG
STORE OSC
    IF LOW ERROR
    IF HIGH ERROR
READ FREQ
    IF LOW ERROR
    IF HIGH ERROR
READ TIMER
    INCREMENT CUT TIMER
        (stored in increments of ¼ secs)
            (but display and store in EEPROM
            in units of minutes . . . round)
            (SAME FOR ALL TIMERS . . .)
SUB VREG (verify voltage regulation)
    MEASURE CURRENT
    SUB AVG
    STORE CUT CURRENT
        IF LOW ERROR
        IF HIGH ERROR
        IF 5% DECREASE FROM AIR CURRENT
        GOTO IDLE MODE
READ FOOT/HAND SWITCH
    IF DEPRESSED GOTO COAG MODE
SUB AUDIBLE INDICATOR - full time while
                          in mode
COAG MODE
READ TARGET
MEASURE VOLTAGE
SUB AVG
STORE VOLTAGE
SUB TRIGGER
SUB VREG (verify voltage regulation)
    MEASURE CURRENT
    SUB AVG
    STORE COAG CURRENT
        IF LOW ERROR

APPENDIX

IF HIGH ERROR
        IF 5% INCREASE IN AIR CURRENT
        GOTO IDLE MODE
MEASURE OSC
SUB AVG
STORE OSC
    IF LOW ERROR
    IF HIGH ERROR
READ FREQ
    IF LOW ERROR
    IF HIGH ERROR
READ TIMER
    INCREMENT COAG TIMER
    IF COAG TIME EXPIRES THEN
        GO TO CUT MODE
SUB AUDIBLE INDICATOR - full time while in mode
INTERRUPTS
60 HZ - STORE CURTCNT & SET GOFLAG (8.33 ms) -
reset trigger
TRIGGER - STORE OUTPUT COMPARE 2 (8.33 ms) -
set trigger
FREQ - INCREMENT ON OVERFLOW (4.61 ms)
PERIOD - STORE FREQ ON OUTPUT COMPARE 1 &
    IMCREMENT ELAPSE TIMERS (250 ms)
SUBS
AVG
TRIGGER
AIR CURRENT - CURRENT AT THE TARGET VOLTAGE
IN AIR TO DETERMINE WHEN KNIFE HAS COM-
PLETED CUT While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims. For example, although the preferred application is in the field of surgical cutting and cautery instruments, the exemplary embodiments contemplate applications where the ultrasonic instrument may be a noncutting cautery instrument or a sonic impact instrument. Additionally, the power demand feature could be applied to nonsurgical fields such as industrial cutting or material separation.

I claim:

1. An ultrasonic surgical apparatus having at least two operating modes, said apparatus comprising:
an instrument for performing a surgical function including cutting and cauterization;
means for transmitting power at an ultrasonic frequency to the instrument at a relatively high level when in a first operating mode wherein the surgical function is to be effected and the load on said instrument is relatively high;
said means also transmitting power to the instrument at a relatively low level in a second operating mode wherein the surgical function is not be effected;
means responsive to said power transmitting means for sensing an electrical parameter with an instantaneous value indicative of a loaded or an unloaded condition wherein, respectively, the instrument is or is not in contact with a medium on which the surgical function is to be performed;
means responsive to said sensing means for operating the means for transmitting in said first operating mode when the instrument is in contact with said medium and for operating the transmitting means in said second mode when the instrument is not in contact with said medium.

2. The apparatus in claim 1 wherein the instrument includes a cutting means.

3. The apparatus of claim 1 wherein the means for transmitting includes means for selecting one of a plurality of high level power settings when in said first operating mode and wherein each setting is a percentage of maximum cutting power.

4. The apparatus of claims 2 or 3 wherein the power applied to the cutting instrument is sufficiently high in said first operating mode as to cause relatively high ultrasonic vibratory movement of said instrument, which results in increased cutting efficiency and a zone of thermal coagulation at the incision.

5. The apparatus as in claim 4 wherein said parameter is driving current.

6. The apparatus of claim 1 further including:
manual switch means;
means responsive to said switch means for causing said means for transmitting to operate in a third mode so as to substantially produce its maximum power output and approximate maximum ultrasonic vibratory movement and maximum heating of said cutting instrument.

7. The apparatus as specified in claim 6 including further means for causing the transmitting means to switch from said third operating mode to said second operating mode when the sensing means indicates that the cutting instrument is not in contact with said medium.

8. The apparatus as in claim 7 wherein said parameter is driving current.

9. The apparatus of claim 8 wherein about a 3% or greater current decrease in the unloaded condition is required to cause said means for transmitting to shift from aid second operating mode to said first operating mode.

10. In an ultrasonic cutting instrument having at least two operating modes, the method of supplying power to said instrument comprising:
transmitting power at an ultrasonic frequency to the cutting instrument at a relatively high level when in a first operating mode wherein cutting is to be effected and the load on said cutting instrument is relatively high;
transmitting power at an ultrasonic frequency to the cutting instrument at a relatively low level in a second operating mode wherein cutting is not to be effected;
sensing an electrical parameter with an instantaneous value which is indicative of a loaded or unloaded condition where, respectively, the cutting instrument is or is not in contact with a medium to be cut;
operating in said first mode when contact with the medium is sensed; and
operating in said second mode when contact with the medium is not sensed.

11. The method of claim 10 wherein said first operating mode includes a plurality of selectable high level power settings each representative of a percentage of maximum cutting power and the method further includes the step of selecting one of said plurality of settings.

12. The method of claims 10 or 11 wherein the power transmitted to the cutting instrument in said first operating mode is sufficiently high as to cause sufficient ultrasonic vibratory movement of said instrument as to result in increased cutting efficiency and increased thermal energy in a localized area of the cutting instrument.

13. The method as specified in claim 10 further including the step of causing power to be transmitted at an ultrasonic frequency to the cutting instrument in a third operating mode so as to substantially produce its maximum ultrasonic vibratory movement and maximum heating of the cutting instrument.

14. The method as specified in claim 13 further including the step of causing the cutting instrument to switch from said third operating mode to said second operating mode when non-contact with said medium is sensed.

15. The method of claim 10 wherein the cutting instrument is a scalpel and the sensed parameter is drive current.

16. The method of claim 15 further including the step of causing the instrument to cease operating in said second mode when about a 3% or greater current decrease is sensed when in the unloaded condition.

17. The method as specified in claim 16 further including the step of causing operation of the instrument in said first mode to cease when the sensed current is approximately 95% or more of a stored maximum threshold value.

18. A process of operating an ultrasonic instrument, said instrument having at least two operating modes, the process comprising the steps of:
operating the instrument in a first power mode wherein the power applied is sufficiently high as to cause the instrument to exhibit ultrasonic vibratory movement;
operating the instrument in a second power mode wherein power is applied at a level sufficient to monitor electrical operating parameters but is sufficiently reduced as to substantially eliminate any ultrasonic vibratory movement;
monitoring an operating parameter which is indicative of whether or not the instrument is in contact with a medium on which the instrument is to operate;
causing the instrument to operate in said first power mode when it is in contact with said medium; and
causing the instrument to operate in said second power mode when it is not in contact with said medium.

19. The method of claim 18 wherein said medium is physiological tissue, said instrument is for use in incising and cauterizing said tissue and wherein the power applied in said first mode is sufficiently high as to produce sufficient vibratory movement to cause an increase in cutting efficiency of the instrument as well as causing a zone of thermal coagulation of the incision which reduces or eliminate bleeding.

20. The method of claim 19 wherein operating the surgical instrument in said first power mode includes the step of selecting one of a plurality of high level power settings wherein each setting is equal to a percentage of maximum cutting power.

21. The process of claim 19 or 20 further including the steps of operating the surgical instrument in a third power mode so as to substantially produce its maximum ultrasonic vibratory movement and maximum heating of said cutting instrument.

22. The process of claim 21 including the further step of causing the operation of the surgical instrument to shift from operating in said third mode to operating in said second mode when loss of contact between the cutting instrument and tissue is detected.

23. The process of claim 20 wherein the operating parameter to be monitored is driving current and a 5% or greater decrease in the non-contact current is required to cause the instrument to begin operating in said first power mode.

24. An ultrasonic apparatus for use in surgical incising and cauterizing of tissue, the apparatus comprising:
   a surgical instrument;
   a power element operative in a first mode of operation to supply driving power to said instrument that is of a sufficient level to cause ultrasonic vibratory movement of the instrument, and operative in a second mode to supply sufficient power to said instrument to monitor electrical operating parameters but insufficient to cause substantial ultrasonic movement of the instrument;
   a feedback network responsive to said power element for detecting said operating parameters;
   a processing circuit responsive to said feedback network for monitoring at least one of said parameters for detecting whether or not said instrument is in contact with tissue,
   said processing circuit causing said power element to operate in said first mode when said tissue contact is detected and in said second mode when no contact is detected.

25. The ultrasonic apparatus of claim 24 wherein said surgical instrument is a scalpel.

26. The ultrasonic apparatus as in claim 25 further comprising an input means connected to said processing circuit for selecting one of a plurality of driving power levels for use in said first mode of operation wherein each of said plurality of levels represents a percentage of maximum cutting power,
   said processing circuit causing said power element to operate at the selected power level when said tissue contact is detected.

27. An ultrasonic apparatus as specified in claim 26 wherein said power element is operative in a third mode of operation to supply substantially maximum driving power so as to substantially produce maximum ultrasonic vibratory movement and maximum heating of said cutting instrument,
   said apparatus further including a manual selection means connected to said processing circuit for causing said power element to operate in said third mode.

28. An ultrasonic apparatus as specified in claim 27 wherein the processing circuit upon detecting no tissue contact will cause said power element to switch from either said first or said third modes to said second mode of operation.

29. An ultrasonic apparatus as specified in claim 28 wherein said parameter for determining whether or not said instrument is in contact with tissue is driving current.

30. The ultrasonic apparatus as specified in claim 29 wherein the processing circuit will cause the power element to shift from said second mode to said first mode of operation only if a 5% of greater decrease in current is sensed.

31. The ultrasonic apparatus as in claim 30 wherein the frequency of the ultrasonic vibratory movement is approximately 55 kilohertz.

32. The ultrasonic apparatus as in claim 31 wherein the ultrasonic driving power delivered in said first mode is sufficiently high at each of the selectable levels as to cause sufficient ultrasonic vibratory movement of the scalpel blade so as to result in increased cutting efficiency as well as producing a narrow zone of white thermal coagulation.

33. The ultrasonic apparatus of claim wherein the power delivered in said third mode of operation causes sufficient heating of the scalpel blade as to obtain white thermal and coaptive coagulation of vessels up to 4 mm in diameter.

34. The ultrasonic apparatus as in claim 33 wherein the processing circuit includes a storage device storing an upper current threshold value and said processor causes the power element to switch to said second mode of operation from said first or third modes of operation when said driving current equals or exceeds said threshold value.

* * * * *